United States Patent
Patel

(10) Patent No.: US 6,306,162 B1
(45) Date of Patent: Oct. 23, 2001

(54) STENT DELIVERY SYSTEM UTILIZING NOVEL BALLOON FOR OBTAINING VARIABLE POST-DEPLOYMENT STENT CHARACTERISTICS

(75) Inventor: Udayan G. Patel, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/461,945

(22) Filed: Dec. 15, 1999

(51) Int. Cl.[7] ............................................. A61F 2/06
(52) U.S. Cl. ................................................. 623/1.11
(58) Field of Search ........................ 623/1.11, 1.12–1.16, 623/1.23; 606/198, 195, 194, 108

(56) References Cited

U.S. PATENT DOCUMENTS

| | | | |
|---|---|---|---|
| 5,807,327 | * 6/2000 | Green et al. ........................ 604/96 |
| 5,913,871 | * 6/1999 | Werneth et al. ..................... 606/194 |
| 5,989,280 | * 11/1999 | Euteneuer et al. .................. 606/198 |
| 6,007,545 | * 12/1999 | Venturelli .......................... 606/108 |
| 6,077,273 | * 6/2000 | Euteneuer et al. .................. 606/108 |

\* cited by examiner

*Primary Examiner*—Henry J. Recla
*Assistant Examiner*—Tan-Uyen T. Ho
(74) *Attorney, Agent, or Firm*—Fulwider Patton Lee & Utecht, LLP

(57) ABSTRACT

A stent delivery system is provided which incorporates a polyurethane balloon which exhibits a high coefficient of friction with respect to metallic substrates. Through the process of stent expansion, the delivery system creates a differential in the rate of axial growth of metallic stents. The differential in growth causes a center portion of the stent to experience greater axial expansion than respective end portions. The stent has the lower axial expansion of the end portions results in a stent having end portions of comparatively higher radial stiffness than the corresponding center portion of the stent.

27 Claims, 3 Drawing Sheets

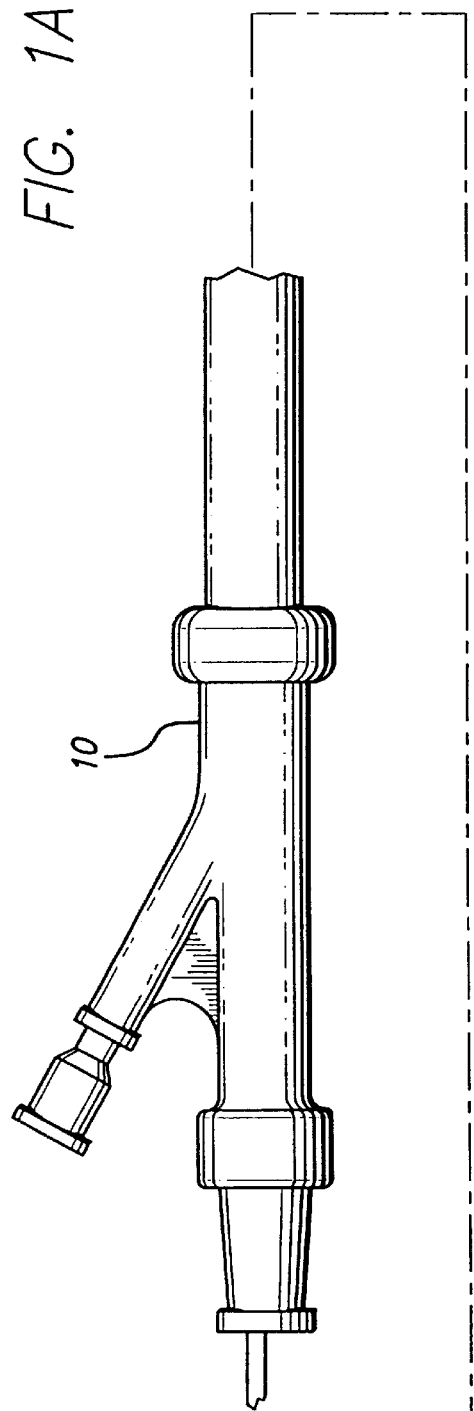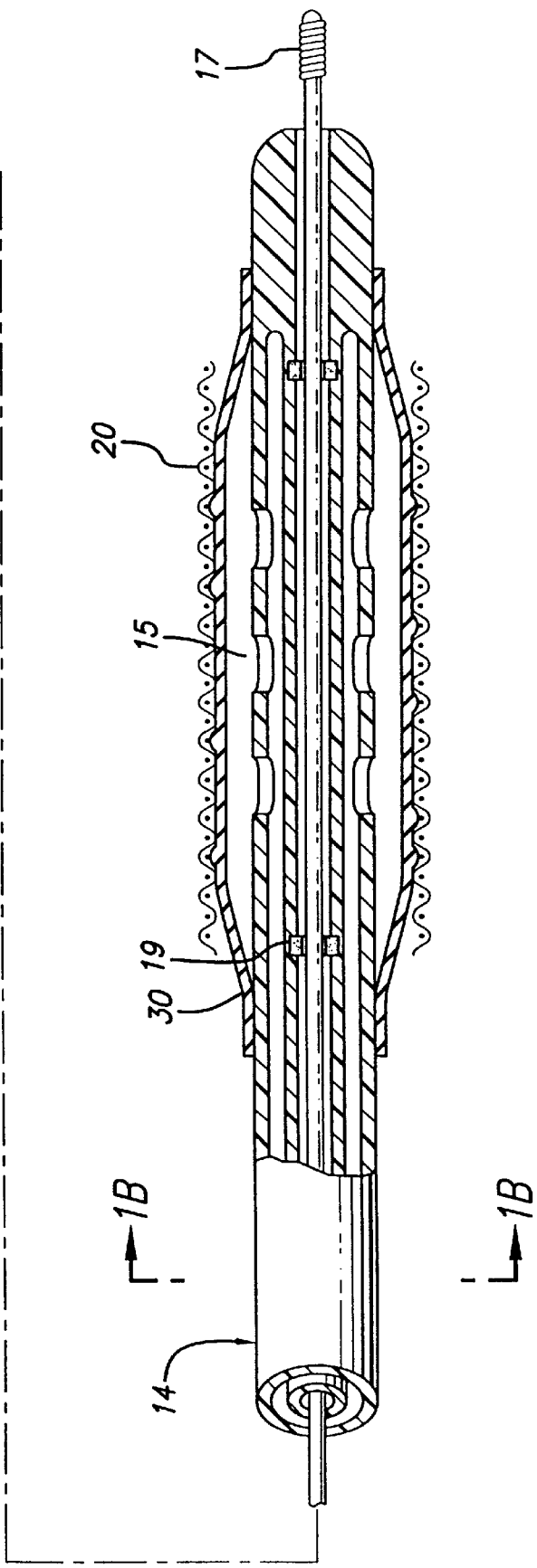
FIG. 1A

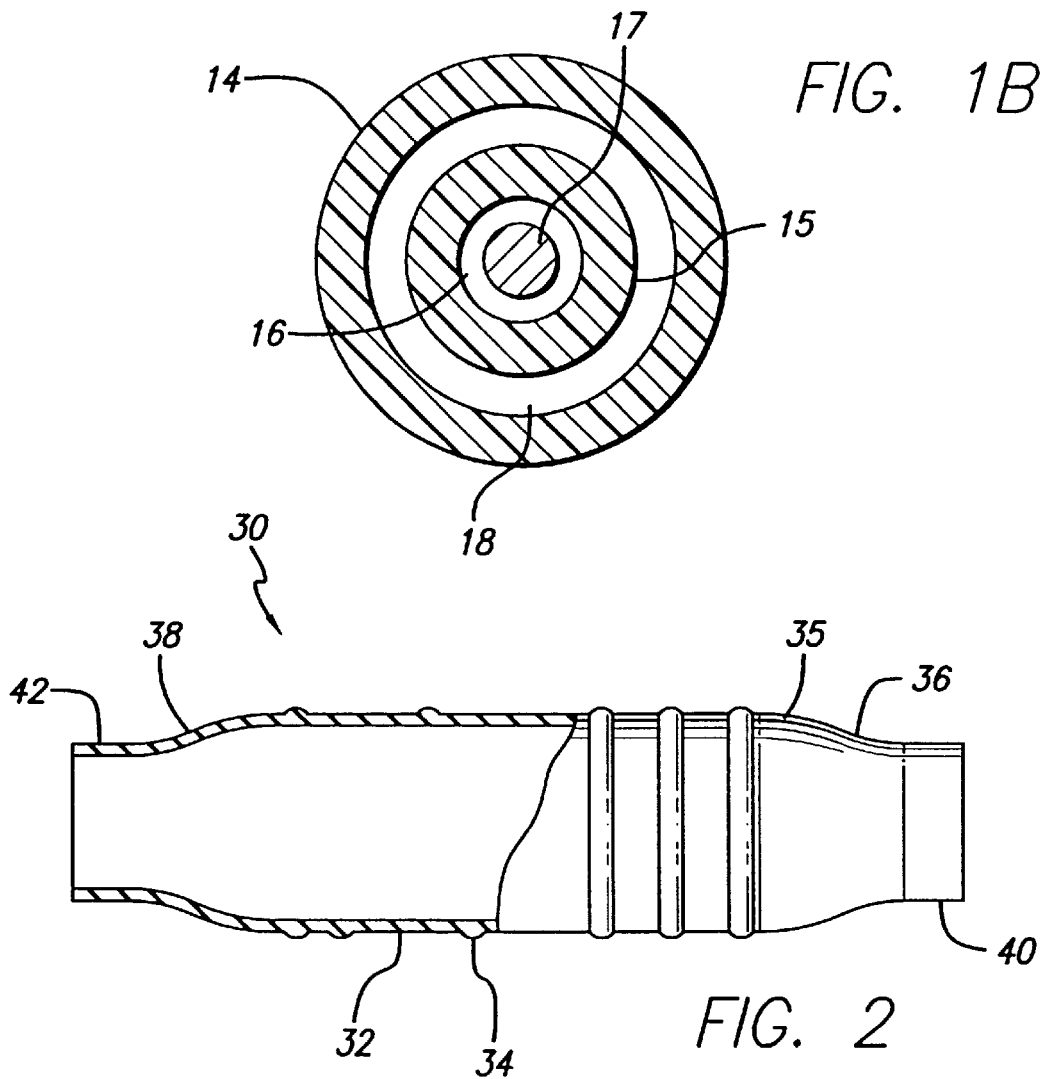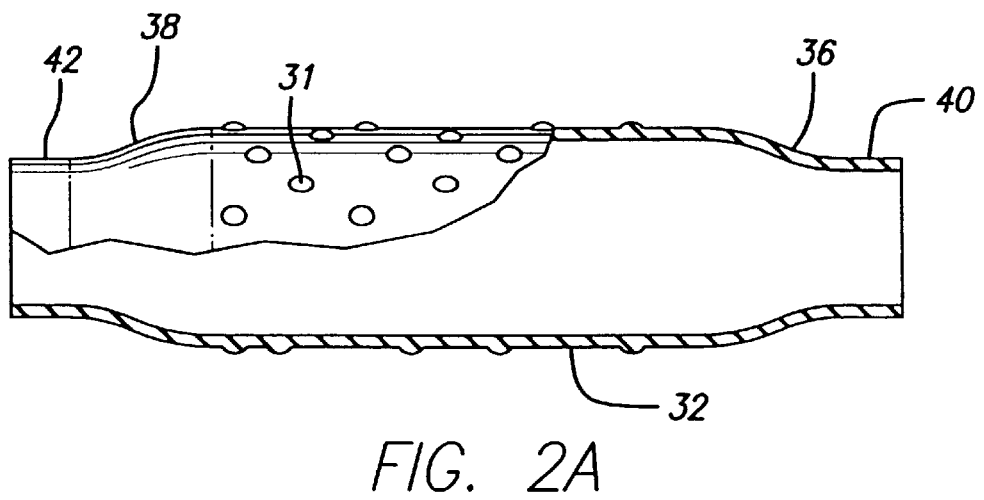

STENT DELIVERY SYSTEM UTILIZING NOVEL BALLOON FOR OBTAINING VARIABLE POST-DEPLOYMENT STENT CHARACTERISTICS

BACKGROUND OF THE INVENTION

The present invention relates to the field of percutaneous transluminal angioplasty generally, and more particularly to a stent delivery system for producing variable post-deployment stiffness characteristics in stents which have uniform pre-deployment radial stiffness.

The use of balloon catheters for high pressure dilation of occluded blood vessels is well known. Balloon coronary angioplasty, for example, is often used as an alternative to open-heart coronary bypass surgery. In a typical balloon angioplasty procedure, a guiding catheter is percutaneously introduced into the cardiovascular system of a patient through the femoral arteries by means of a conventional Seldinger technique and advanced within a patient's vascular system until the distal end of the guiding catheter is positioned at a point proximal to the lesion site. A guidewire and a dilatation catheter having a balloon on the distal end are introduced through the guiding catheter with the guidewire sliding within the dilatation catheter. The guidewire is first advanced out of the guiding catheter into the patient's vasculature and is directed across the arterial lesion. The dilatation catheter is subsequently advanced over the previously advanced guidewire until the dilatation balloon is properly positioned across the lesion. Once in position, the expandable balloon is inflated to a predetermined size with a radiopaque liquid at relatively high pressures, usually in the range of about 6–12 atmospheres. Balloon expansion radially compresses the atherosclerotic plaque of the lesion against the inside of the artery wall and thereby dilates the lumen of the artery. The balloon is then deflated to a small profile so that the dilatation catheter may be withdrawn from the patient's vasculature and blood flow resumed through the dilated artery. As should be appreciated by those skilled in the art, while the above-described procedure is typical, it is not the only method used in angioplasty.

Balloon angioplasty sometimes results in short or long term failure. That is, vessels may abruptly close shortly after the procedure or gradual restenosis may occur up to several months afterward. To counter the tendency of recurrent vessel occlusion following angioplasty, implantable intravascular prostheses, commonly referred to as stents, have emerged as a means by which to achieve long term vessel patency. Stated simply, a stent functions as permanent scaffolding to structurally support the vessel wall and thereby maintain luminal patency. Stents are typically small tubular metallic structures.

Since the present invention is directed to an improved stent delivery system, it may prove useful to briefly describe the components and operation of a typical stent delivery system. Such systems typically include a balloon catheter, a stent which is mounted on the balloon, and a delivery sheath which surrounds the stent-delivery catheter. Initial angioplastic dilation of the lesion produces a residual lumen large enough to accept the stent delivery system. The guiding catheter used to perform the initial dilation is typically left in place in the patient and reused during the stent implantation procedure. The stent-delivery catheter is routed through the guiding catheter to a position in which its distal end is disposed substantially coextensively with the distal end of the guiding catheter and immediately proximate of previously expanded lesion.

Once properly positioned relative to the guiding catheter, the stent-carrying catheter is extended from the distal end of the guiding catheter until the stent spans the previously dilated lesion. The delivery sheath which is slidable relative to the delivery catheter, balloon and stent, is then withdrawn into the guiding catheter to expose the balloon and stent. The delivery catheter is then supplied with a pressurized fluid, which expands the balloon and associated stent to a desired diameter sufficient to exceed the elastic limit of the stent. The stent thus comes in contact with, and permanently supports, the wall of the vessel. The delivery catheter balloon is then deflated and the delivery catheter and guiding catheter are withdrawn, leaving the expanded stent supporting the vessel lumen.

Prior art stent delivery systems have generally proven to be effective. However, in the treatment of certain vascular diseases, it is desirable to have a stent with reinforced end rings or regions of relatively high stiffness at one or both ends of the stent. Such a stent is required to successfully treat ostial vessel diseases such as in the renal vessels. The ostium of the renal vessels requires a stent with an end region which possesses relatively high resistance to radial compression. This is due to the close proximity of the aortic wall muscles which have a tendency to contract around the renal ostium and which may cause radial collapse of a dilated vessel implanted with a non-reinforced stent. Vessels such as the coronary sinus, ostial RCA, and ostial left main, and other vessels where the ostium is surrounded by tissue which produces high radial forces, may also be beneficially treated by a stent with a reinforced or high stiffness end region. Stents of this type are commonly referred to as variable stiffness stents. The present invention satisfies these and other needs.

SUMMARY OF THE INVENTION

The present invention provides a stent delivery system that utilizes a conventional dilatation catheter, equipped with a novel polyurethane inflation balloon, in combination with any one of several types of commercially available stents. The system creates a stent which would otherwise have uniform radial stiffness in its expanded state into a stent having comparatively high stiffness end portions or reinforced rings in its expanded state. The catheter of the present invention includes an elongated body having proximal and distal ends and an inflation balloon disposed proximate to the distal end of the catheter. The catheter further includes a port in its proximal end and an inner lumen between the port and the balloon. The port is in fluid communication with the balloon and supplies high pressure radiopaque fluid to the interior cavity of the balloon for balloon inflation. The balloon of the present invention can be formed from polyurethane material which possess a high coefficient of friction when bearing against metallic materials. The balloon includes a cylindrical working portion with end portions of selected taper. The balloon is designed to have relatively high axial compliance in comparison to its radial compliance. Stents suitable for use with the delivery system of the present invention include all stents having a closed cellular structure in their expanded state.

The stent delivery system of the present invention is used with a stent of sufficient length such that the ends of the stent overhang the tapered portions of the balloon when the stent is centered on the balloon. The stent delivery system of the present invention is able to utilize balloon axial growth under high pressure and the high frictional resistance of the selected polyurethane material to produce substantial longitudinal expansion over a center portion of the stent, while the overhanging ends of the stent experience minimal longitudinal expansion. The central portion and end portions of the stent experience the same degree of radial expansion by the end of the expansion process. The differential in the rate of longitudinal expansion produces comparatively low cell density in the expanded center portion of the stent and comparatively high cell density in the expanded end portions of the stent. The comparatively high cell density in the end portions corresponds to a comparatively higher degree of radial stiffness.

Other features and advantages of the present invention will become apparent from the following detailed description.

BRIEF DESCRIPTION OF THE DRAWINGS

FIG. 1 is a side view, partially in section, depicting one embodiment of the stent delivery system of the present invention.

FIG. 1A is a cross-sectional view taken along line 1A—1A depicting the inner and outer tubular members of the catheter shown in FIG. 1.

FIG. 2 is a cross-sectional view of one particular embodiment of a balloon made in accordance with the present invention.

FIG. 2A is a partial cross-sectional view of one particular embodiment of a balloon made in accordance with the present invention.

DETAILED DESCRIPTION OF THE PREFERRED EMBODIMENTS

Figure 3:
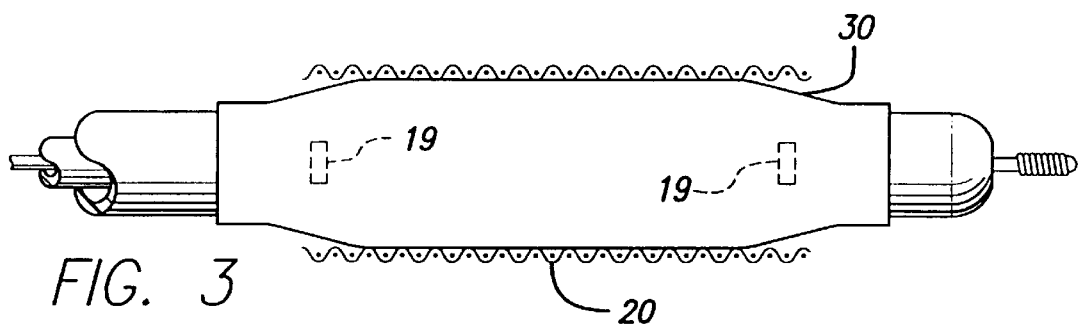
FIG. 3 is a partial sectional view of the distal end of the stent delivery system shown in FIG. 1 depicting the catheter balloon, in its folded configuration, with a stent mounted thereon.

The present invention has a novel construction of an inflation balloon designed to utilize the properties of selected polyurethane materials to produce a balloon with high axial compliance, moderate radial compliance, and high adherence to metallic substrates. Catheter balloons are usually classified in terms of radial compliance, with balloons typically being classified as having low, medium, or high compliance. Radial compliance, as the term is used in the art, refers to the increase in a balloon's diameter over the balloon's nominal diameter at low inflation pressure. Balloon compliance is primarily a function of balloon material. Catheter balloons are most commonly made from polyester, polyamide, and polyolefin materials. Balloons made from polyester materials typically exhibit low compliance. Low compliance balloons generally increase in diameter at the rate of 0.1 mm per atmosphere pressure. Balloons made from polyamide materials typically have medium compliance. Medium compliance balloons increase in diameter at the rate of about 0.2–0.3 mm per atmosphere pressure. Balloons made from Polyolefin materials typically exhibit the highest degree of compliance. High compliance balloons increase in diameter at a rate of about 0.3–1.0 mm per atmosphere pressure.

Axial compliance, or the tendency of the balloon to elongate along the balloons longitudinal axis, has heretofore not been considered a significant factor affecting stent deployment. Polyester, polyamide, and polyolefin materials all exhibit a very low coefficient of friction, in the range of 0.30 to 0.40, when bearing against a metallic structure such as a stainless steel stent. Although balloons produced from the above mentioned materials are effective in producing radial expansion of a stent, they usually do not adhere very well to metallic stents and therefore merely slip underneath the stent as they grow axially during expansion. Thus, these materials have little or no effect on the post expansion length of metallic stents.

Recent work with polyurethane materials has revealed that balloons constructed of this material can be tailored to have medium radial compliance in the range of 0.3 mm diametrical growth per atmosphere pressure and relatively high axial compliance in the range of 0.4 mm longitudinal growth per atmosphere pressure. In addition, polyurethane materials have demonstrated strong surface adhesion to metal substrates. Polyurethane materials have demonstrated coefficients of friction in the range of about 0.4 to 0.7 in bearing against metallic substrates such as stainless steel. When a metallic stent is mounted on a polyurethane balloon, the balloon material adheres much better to the stent than other polymeric materials and thereby forces the stent to grow axially as well as radially, during expansion.

The ability of polyurethane materials to force a stent to grow axially may be used to advantage in forming a variable stiffness stent. By selecting a stent with an overall length such that the ends of the stent extend axially outwardly over the tapered portions of the catheter balloon, a differential in the rate of axial growth of the stent may be created. More specifically, at low to medium inflation pressure the center portion of the stent which is in contact with the cylindrical working portion of the balloon grows axially as the balloon is expanded. Stent axial growth in the range of 0.4 mm per atmosphere pressure is achievable with Multilink type stents. As a result, the expanded cells of the center portion of the stent are more widely spaced than those of the end portions, which due to their position overhanging the tapered portions of the balloon, experience little or no axial growth and consequently have closer cell spacing at full expansion. The closer cell spacing at full expansion provides the end portions of the stent with a higher degree of radial stiffness in comparison to the radial stiffness of the center portion. Stents expanded with polyurethane balloons have an increased end stiffness of about 10% over the stiffness of the center portion of the stent.

The catheters used in the present invention are most conveniently constructed as over-the-wire balloon catheters of conventional form for use in angioplasty, except that the balloon has an exterior working surface of high frictional resistance. However, it should be appreciated that the present invention may also be applied to fixed wire catheters, rapid exchange type catheters, and other non over-the-wire catheters.

FIG. 1 illustrates a stent delivery system that embodies features of the invention. Generally, the delivery system comprises a catheter 10, which includes an expandable member, such as an inflatable balloon 30, and a stent 20 mounted on the balloon 30. Referring now to FIGS. 1 and 1A, the balloon catheter 10 includes an elongated outer tubular member 14 and an elongated inner tubular member 15 coaxially disposed within the outer tubular member 14. The inner tubular member 15 has an inner lumen 16 adapted to receive a guidewire 17. The inner tubular member 15 and the outer tubular member 14 define an annular lumen 18 which directs inflation fluid to the interior of the balloon 30. The inner tubular member 15 is equipped with radiopaque markers 19, which are positioned radially in line with ends of the mounted stent 20, to aid a vascular surgeon when placing the catheter 10 within a blood vessel. The dimensions of the intravascular catheter for use in the present invention will generally follow the dimensions of intravascular catheters used in angioplasty procedures in the same arterial location. For example, in angioplasty procedures involving the coronary arteries, catheters are typically about 150 cm long with an outer diameter of about 0.89 mm. Materials for and methods of manufacturing such catheters are well known to those skilled in the art.

Referring now to FIG. 2, the balloon 30 has an elongated cylindrically shaped working portion 32. On opposing ends of the working portion 32 are the tapered portions 36 and 38. A shoulder 35 is defined by the junction between the working portion 32 and the tapered end portions 36 and 38. The skirts or waists 40 and 42 are provided respectively on the small diameter end of the tapered portions 36 and 38. In circumstances where greater frictional force is needed for a stent to expand axially, the working portion 32 may be optionally equipped with a plurality of integrally formed ridges 34 which serve to form points of high frictional resistance between the balloon and a metallic stent, as shown in FIG. 2. The same purpose may also be achieved by adding a pebble grain texture 31 to the working portion of the balloon 32, as shown in FIG. 2A. As illustrated in the drawings, the working portion 32 and the tapered portions 36 and 38 have essentially the same wall thickness. By keeping the wall thickness of the tapered portions essentially the same as that of the working portion, the tapered portions, when subjected to high pressure, will expand inline with the working portion. The skirts 40 and 42 need not, and generally do not, have the same wall thickness as the working section 32 and the tapered sections 36 and 38. The distal skirt 40 of the balloon 30 is attached to the distal end of the inner tubular member 15 of the catheter 10. The proximal skirt 42 is attached to the outer tubular member 14. Suitable means for attaching the skirts 40 and 42 to the catheter 10 include heat welding, solvent welding, ultrasonic welding, and adhesive bonding. Several types of polyurethane are suitable for making the balloons for use in the present invention. The type of polyurethane chosen is dependant on the amount of axial elongation desired at the center portion of the stent and the desired maximum inflation pressure. The coefficient of friction of the polyurethane balloon is in part a function of the balloon hardness. Generally, polyurethanes with a surface hardness of about 75 durometer (Shore A) to about 80 durometer (Shore D) are preferred. The maximum inflation pressure of the balloon is function of the balloon's geometry, wall thickness, and of the material's tensile strength. Polyurethanes typically have an ultimate tensile strength within a range of about 4500 psi to about 9000 psi, which is sufficient for the production of high pressure balloons. Thermoplastic polyurethanes, such as those synthesized from d-isocycinates, are particular well suited for making balloons for use in the present invention. One example of a suitable commercially available polyurethane is PELLETHANE 2633-75D, which is sold by the DOW Chemical Corporation.

The balloon of the present invention may be made using any conventional process, such as blow molding or extrusion. The actual dimensions of the balloon 30 will depend upon the particular dilation procedure for which the balloon and catheter are to be employed. In general, when the balloon is for angioplasty usage, the external diameter of the balloon will be of the order of about 1 mm to about 25 mm. The overall length of the inflated portion will be on the order of about 10 mm to about 150 mm. The walls of the balloon will have an average thickness of about 0.01 mm to about 0.2 mm depending in part on the pressures to which the balloon will be inflated. The dimensions and methods given above are exemplary only and are not to be construed as limiting.

The stent employed with the device of the present invention should ideally be formed of a metallic material and have a closed cell structure in its expanded state. Co-owned U.S. Pat. No. 5,514,154 to Lau et al., U.S. Pat. No. 5,569,295 to Lam, U.S. Pat. No. 5,591,197 to Orth et al., U.S. Pat. No. 5,603,721 to Lau et al., U.S. Pat. No. 5,649,952 to Lam, U.S. Pat. No. 5,728,158 to Lau et al., and U.S. Pat. No. 5,735,893 to Lau et al. describe suitable stents, and these patents are hereby incorporated herein in their entirety by reference hereto. The above list is exemplary and is not inclusive. Other stent designs and designs utilizing non-metallic materials are also suitable.

Referring now to FIGS. 3–6, the stent delivery system of the present invention is used as follows. With reference to FIG. 3, in order to create high stiffness end portions, the stent 20 is selected such that the length of the stent is greater than that of the working section 32 of the balloon 30. The stent is then positioned on the folded balloon 30 such that the ends of the stent overhang the respective tapered portions 36 and 38 of the balloon. In most applications, it is desirable to center the stent on the folded balloon, as is illustrated in FIG. 3, whereby the stent's proximal and distal ends equally overhang the respective tapered portions of the balloon. However, in some situations where it is desired to create a stent with only one high stiffness end, a stent may be positioned such that only one end overhangs a tapered portion of the balloon. Once the stent 20 is positioned on balloon 30, the stent is crimped into place. There are many varieties of suitable crimping tools known to those skilled in the art which can be utilized to crimp the stent into place.

Once the stent 20 has been positioned and crimped onto the catheter balloon 30, the stent-bearing catheter 10 is then advanced through a body lumen to a lesion site by conventional medical techniques. Generally, a guiding catheter is first placed in the patient's vasculature and advanced through the body lumen to a point proximal of the lesion site. A guidewire 17 is then advanced through the guiding catheter and is advanced out of the guiding catheter across the lesion site to a point distal of the lesion. The catheter-stent assembly 10 is subsequently advanced over the guidewire until the stent 20 is positioned across the lesion site. The balloon 30 of the catheter 10 is then inflated, whereby the stent 20 begins to expand.

Figure 4:
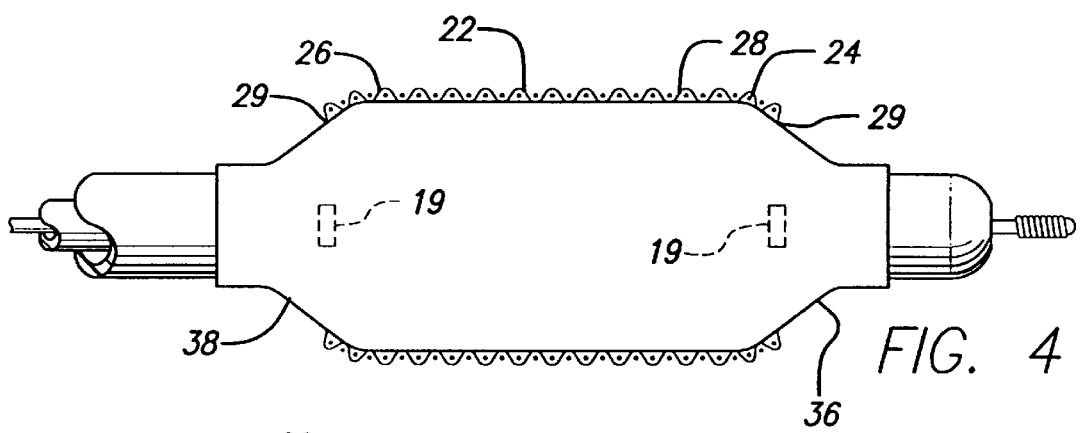
FIG. 4 is a partial sectional view of the distal end of the stent delivery system shown in FIG. 1 depicting the catheter balloon, inflated at low pressure, with a stent mounted thereon.

Referring now to FIG. 4, initial inflation of the balloon at low pressure, corresponding to a range of 2–4 atmospheres, generates a small degree of radial and axial stent expansion. As a result of this low pressure inflation, the stent forms a discrete center portion 22 which is substantially coextensive with the working portion of the balloon 32. In addition, the stent forms discrete proximal and distal tapered portions 26 and 24 respectively. The tapered portions 26 and 24 of the stent 20 substantially conform to the tapered portions 38 and 36 of the balloon 30. At this point only minimal expansion of the stent's cellular structure has occurred.

Figure 5:
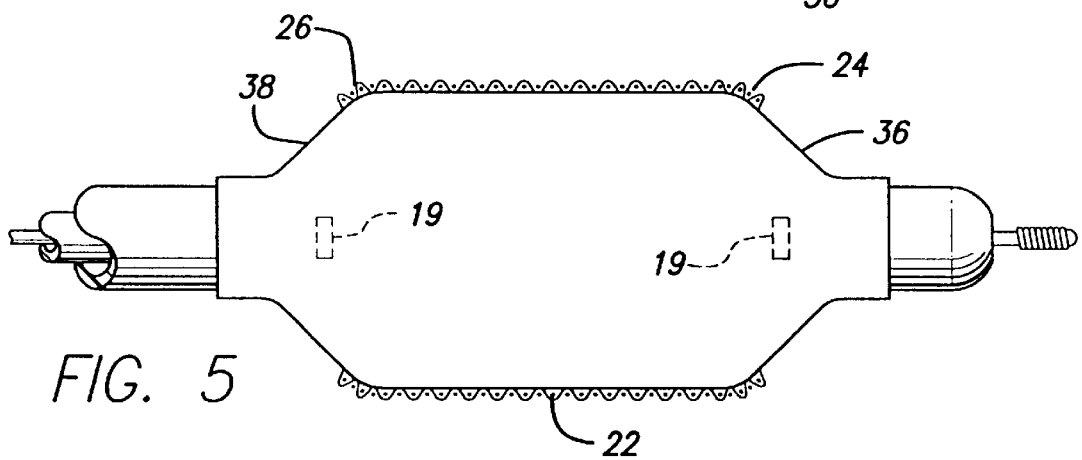
FIG. 5 is a partial sectional view of the distal end of the stent delivery system shown in FIG. 1 depicting the catheter balloon, inflated at moderate pressure, with a stent mounted thereon.

Referring now to FIG. 5, at moderate pressure, in the range of 6–8 atmospheres, the balloon extends longitudinally. Consequently, due to the high frictional resistance between the balloon and the stent, the center portion of the stent 22 expands longitudinally essentially the same amount as the working portion 32 of the balloon 30. As shown in FIG. 5, the cell density 28 of the stent in the center portion 22 has decreased relative to the cell density 29 of the end portions 24 and 26 which have experienced minimal longitudinal expansion.

Figure 6:
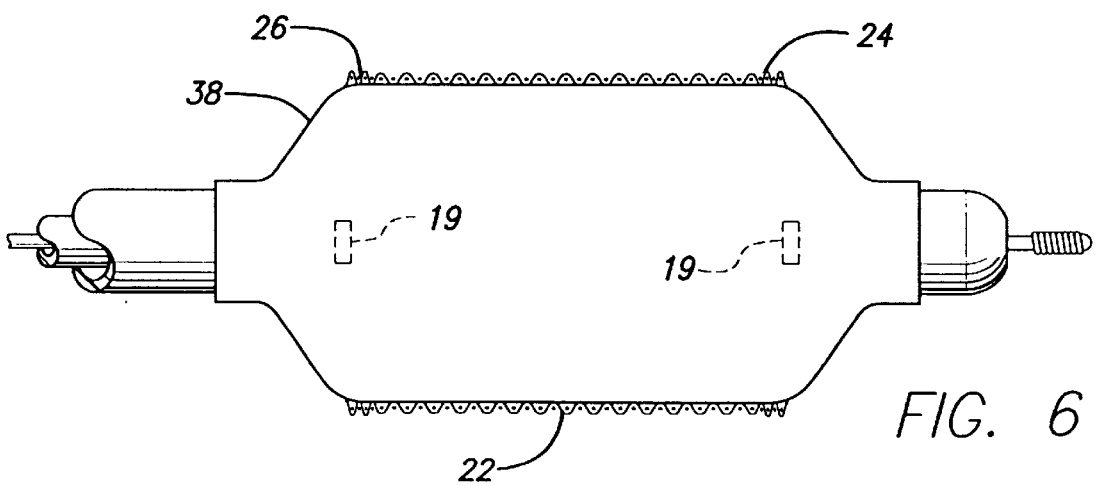
FIG. 6 is a partial sectional view of the distal end of the stent delivery system shown in FIG. 1 depicting the catheter balloon, inflated at maximum pressure, with a stent mounted thereon.

Referring now to FIG. 6, at a maximum pressure of about 15 atmospheres, the tapered end portions 36 and 38 of the balloon 30, expand fully with the working portion 32, whereby the end portions 26 and 24 of the stent 20 are fully expanded radially to the same diameter as the center section 22. As the end portions 24 and 26 are deformed upwardly, a minimal amount of longitudinal expansion occurs. Thus, at the end of the expansion process, the end portions 24 and 26 of the stent have a cell density relatively higher than the center portion 22. Thus, the differential in axial expansion between the center section 22 and the end portions 24 and 26 of the stent 20 effectively forms a stent with high cell density and stiffness at the end portions 24 and 26.

It will be appreciated that a new device and method for creating a variable stiffness stent has been presented. While only the presently preferred embodiment has been described in detail, as will be apparent to those skilled in the art, modifications and improvements may be made to the device and method disclosed herein without departing from the scope of the invention. Accordingly, it is not intended that the invention be limited except as by the appended claims.

What is claimed is:

1. A stent delivery system for delivering an expandable stent within a body lumen, comprising:

an elongated tubular catheter having proximal and distal ends and an expandable member attached proximally to the distal end of the catheter for mounting of an expandable stent;

the catheter having an inflation lumen with the proximal end of the catheter being in fluid communication with the expandable member through the inflation lumen;

the expandable member including a cylindrical working portion which is expandable in a radial and axial direction and a tapered end portion at each end of the cylindrical working portion;

a stent having a central portion and a pair of end portions, wherein the center portion of the stent is placed on the working portion and the end portions of the stent are placed over the tapered end portions of the expandable member; and the expandable member being made from polyurethane material having a high coefficient of friction in bearing against metallic substrates to cause the center portion of the stent to expand radially and axially with the working portion of the expandable member when expanded while the tapered end portions permit radial expansion but little or no axial expansion of the remainder of the stent.

2. The stent delivery system of claim 1 wherein the cylindrical working portion of the expandable member includes a plurality of integrally formed ridges, whereby the ridges form points of high frictional resistance to engage and securely hold the expandable stent on the expandable member.

3. The stent delivery system of claim 1 wherein the cylindrical working portion of the expandable member includes a pebble grain texture, whereby the pebble grain texture forms a surface of high frictional resistance to engage and securely hold the expandable stent on the expandable member.

4. The stent delivery system of claim 1 wherein the polyurethane material exhibits a coefficient of friction in the range of 0.4 to 0.7 in bearing against metallic substrates.

5. The stent delivery system of claim 1 wherein, the polyurethane material exhibits a coefficient of friction in the range of 0.4 to 0.7 in bearing against a stainless steel substrate.

6. The stent delivery system of claim 1 further including radiopaque markers positioned radially in line on the catheter with a shoulder defining a junction where each of the tapered end portions of the expandable member is joined with the working portion of the expandable member.

7. The stent delivery system of claim 1 wherein the expandable stent is made from a metallic material.

8. A method of delivering and deploying an expandable stent to a desired location within a body lumen, the stent having variable radial stiffness in the expanded state, comprising the steps of:

providing a dilatation catheter, the dilatation catheter having an expandable member with tapered end portions and a cylindrical center portion therebetween, which is proximal to the distal end of the dilatation catheter;

providing an expandable intravascular stent;

mounting the stent on the expandable member wherein a central portion of the stent is disposed over the cylindrical portion of the expandable member and at least one end portion of the stent extends outwardly over a tapered portion of the expandable member;

advancing the dilatation catheter with the stent mounted on the expandable member though the body lumen to a selected location within the body lumen;

expanding the expandable member at moderate pressure to allow the central portion of the expandable member to expand radially to a select diameter and longitudinally while the end portion of the stent expands minimally, conforming to the tapered end portion of the expandable member;

expanding the expandable member at a higher pressure to allow the tapered ends of the expandable member to expand fully to be flush with the central portion of the expandable member, which expands the end portion of the stent to the select diameter, with minimal longitudinal expansion; and deflating the expandable member and withdrawing the dilatation catheter from the body lumen.

9. The method of claim 8, wherein the stent has a sufficient length which allows each end of the stent to project over each tapered end portion of the expandable member when the stent is centered on the expandable member.

10. The method of claim 8 wherein the step of mounting the stent on the expandable member includes centering the stent such that each end of the stent extends over a tapered end portion of the expandable member.

11. The stent delivery system of claim 1, wherein the expandable member is a balloon.

12. The stent delivery system of claim 1, wherein the end portions of the stent do not touch the tapered end portions of the expandable member when placed on the expandable member when in an unexpanded condition.

13. A stent delivery system for delivering an expandable stent within a body lumen, comprising:

a catheter having an expandable member attached thereto for mounting of an expandable stent, the expandable member including a working portion which is expandable in a radial and axial direction and a tapered end portion at each end of the working portion;

a stent having a central portion and a pair of end portions, wherein the center portion of the stent is placed on the working portion and the end portions of the stent are placed over the tapered end portions of the expandable member, the expandable member having a high coefficient of friction in bearing against the stent to cause the center portion of the stent in contact with the working portion to expand both radially and axially when the expandable member is expanded while the tapered end portions permit radial expansion but little or no axial expansion to the remainder of the stent.

14. The stent delivery system of claim 13, wherein the end portions of the stent do not touch the tapered end portions of the expandable member when placed on the expandable member when in an unexpanded condition.

15. The stent delivery system of claim 14, wherein during expansion of the expandable member, the end portions of the stent contact the tapered end portions to allow the end portions of the stent to be radially expanded.

16. The stent delivery system of claim 13, wherein the working portion of the expandable member includes a plurality of integrally formed ridges, whereby the ridges form points of high frictional resistance to engage and securely hold the stent on the expandable member.

17. The stent delivery system of claim 13, wherein the working portion of the expandable member includes a pebble grain texture, whereby the pebble grain texture forms a surface of high frictional resistance to engage and securely hold the stent on the expandable member.

18. The stent delivery system of claim 13, wherein the expandable member is made from a polyurethane material having a coefficient of friction in the range of 0.4 to 0.7 in bearing against a metallic substrate.

19. The stent delivery system of claim 13, wherein the expandable member is made from a polyurethane material having a coefficient of friction in the range of 0.4 to 0.7 in bearing against a stainless steel substrate.

20. The stent delivery system of claim 13, further including radiopaque markers positioned radially in line on the catheter with a shoulder defining a junction where each of the tapered end portions of the expandable member is joined with the working portion of the expandable member.

21. The stent delivery system of claim 13, wherein the stent is made from a metallic material.

22. The stent delivery system of claim 13, wherein the expandable member is a balloon.

23. The stent delivery system of claim 13, wherein the working portion of the expandable member is shorter than the stent to be mounted thereon.

24. The stent delivery system of claim 13, wherein the working portion of the expandable member is shorter than the stent.

25. A method of delivering and deploying a stent to a desired location within a body lumen, comprising:

providing a delivery catheter with an expandable member having a central working portion and a pair of tapered end portions;

mounting a stent having a central portion and a pair of end portion on the expandable member wherein the central portion of the stent is disposed over the central working portion of the expandable member and at least one end portion of the stent extends outwardly over a tapered end portion of the expandable member;

advancing the delivery catheter with the stent mounted on the expandable member though the body lumen to a selected location within the body lumen;

expanding the expandable member at moderate pressure to allow the central working portion of the expandable member to expand the center portion of the stent radially to a select diameter and longitudinally while the end portions of the stent expand minimally, conforming to the tapered end portions of the expandable member;

expanding the expandable member at a higher pressure to allow the tapered end portions of the expandable member to expand fully to be flush with the central working portion of the expandable member, which radially expands the end portions of the stent to the select diameter with minimal longitudinal expansion; and deflating the expandable member and withdrawing the delivery catheter from the body lumen.

26. The method of claim 25, wherein the stent has a sufficient length which allows each end portion of the stent to project over each tapered end portion of the expandable member when the stent is centered on the expandable member.

27. The method of claim 25, wherein the mounting of the stent on the expandable member includes centering the stent such that each end portion of the stent extends over a tapered end portion of the expandable member.

* * * * *